United States Patent [19]

Lasky

[11] 4,051,380

[45] Sept. 27, 1977

[54] APPARATUS AND METHOD FOR SUPPORTING AND POSITIONING THE BODY TO FACILITATE RADIOGRAPHIC MAMMOGRAPHY PROCEDURES

[76] Inventor: Harold J. Lasky, 2756 Euclid Park Place, Evanston, Ill. 60202

[21] Appl. No.: 672,303

[22] Filed: Mar. 31, 1976

[51] Int. Cl.² .............................................. G03B 41/16
[52] U.S. Cl. .................................. 250/451; 250/444; 250/456
[58] Field of Search .............. 250/444, 439, 446, 451, 250/456, 490, 491

[56] References Cited

U.S. PATENT DOCUMENTS

| | | | |
|---|---|---|---|
| 3,396,274 | 8/1968 | Hogan | 250/456 |
| 3,556,081 | 1/1971 | Jones | 250/446 |
| 3,578,971 | 5/1971 | Lasky | 250/456 |
| 3,708,662 | 1/1973 | Kurokawa et al. | 250/446 |
| 3,806,109 | 4/1974 | Weber et al. | 250/439 |
| 3,824,397 | 7/1974 | Bauer et al. | 250/491 |
| 3,831,032 | 8/1974 | Putod | 250/451 |
| 3,971,950 | 1/1976 | Evans et al. | 250/451 |
| 3,973,126 | 8/1976 | Redington et al. | 250/444 |

Primary Examiner—Alfred E. Smith
Assistant Examiner—B. C. Anderson
Attorney, Agent, or Firm—Kegan, Kegan & Berkman

[57] ABSTRACT

A stretcher-like table or cradle for use as a body support during radiological examination. The table includes means whereby it may be arcuately pivotally manipulated about each of two mutually perpendicular horizontal axes. For specific uses in mammographic procedures, the support surface or web of the table is provided with a cut-away areal zone through which the gravitationally suspended breast of the female subject depends. Selective and controlled pivotal tilting of the table makes precise orientational positioning of the suspended tissue feasible, so as to provide improved fidelity and enhanced diagnostic value for the radiographic film images produced.

19 Claims, 7 Drawing Figures

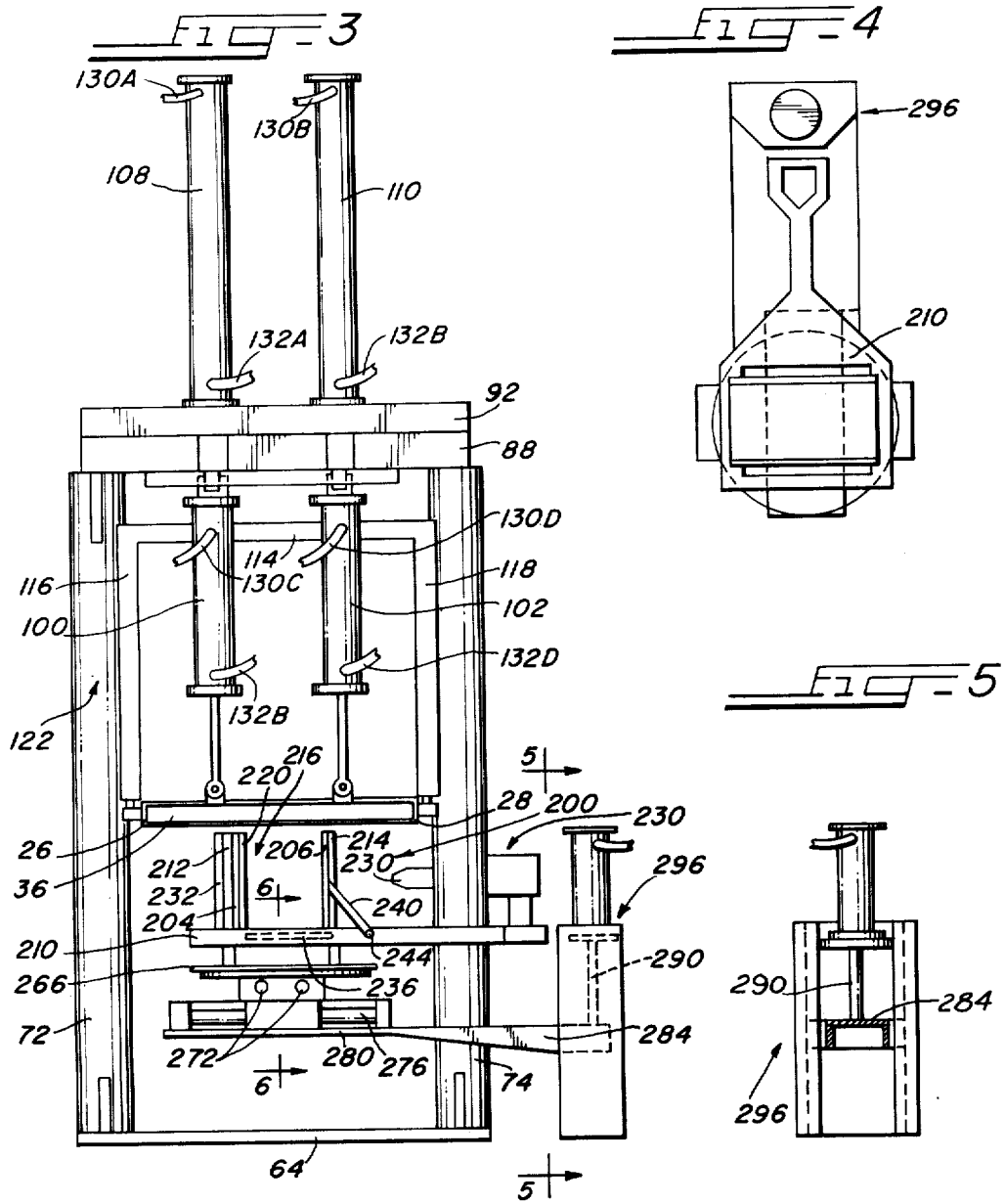
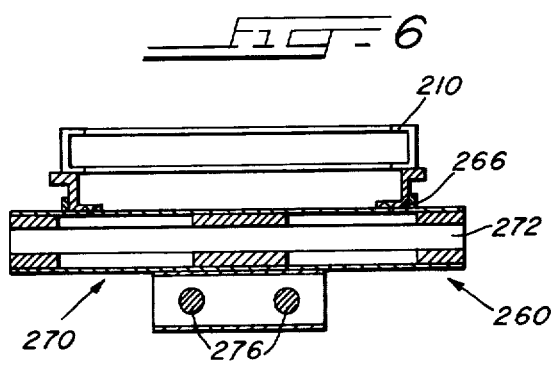

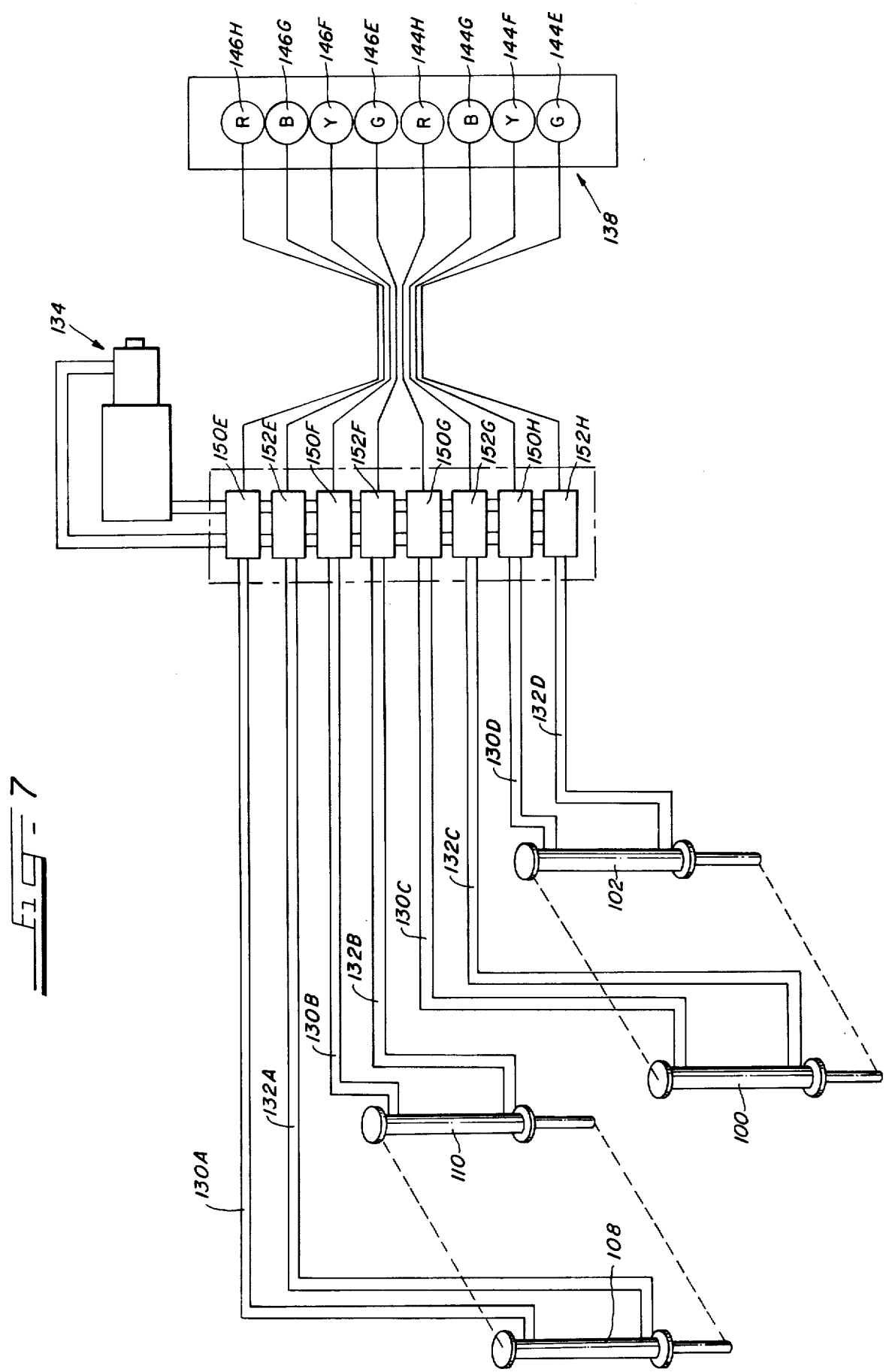

APPARATUS AND METHOD FOR SUPPORTING AND POSITIONING THE BODY TO FACILITATE RADIOGRAPHIC MAMMOGRAPHY PROCEDURES

BACKGROUND OF THE INVENTION

The present invention relates to apparatus and methods for medical radiographic examination. More particularly, the invention is directed to improved apparatus and techniques for carrying out diagnostic X-ray examinations and for detecting internal growths including tumors, cancer and other types of defects and abnormalities. Specifically, the invention describes an improved body-supporting apparatus for the selective and controlled orientational positioning of a subject so as to provide improved fidelity and enhanced diagnostic value for the radiographic film images produced, particularly in mammography.

The subject invention augments and is an improvement over the technique and apparatus described in Harold J. Lasky U.S. Pat. No. 3,578,971 for Mammographic X-ray Apparatus and Technique, and the entire disclosure of that patent is hereby specifically incorporated herein by reference to the extent it is not inconsistant herewith.

Radiographic examination procedures have been widely used in the past for medical diagnosis and to detect tumorous body growths. In the specific application known as mammography, the techniques have been applied to the detection of breast tumors, cancer, and other growths, in the adult female breast. In widely employed prior art diagnostic procedures it has been necessary to expose the subject to relatively large quantities of radiation. Additionally, for the most part, prior art techniques have failed to distinguish non-palpable growths in spite of the use of such excessively high radiation levels.

Lasky U.S. Pat. No. 3,578,971 referred to above describes an improved method for X-ray examination of the breast of a female subject under conditions which permit minimal radiation exposure and ensure optimum fields of examination, sharp image focus, and even image density. A substantive feature of the technique is the carrying out of the radiographic examination while gently yet firmly compressing the breast of a female subject, while the breast is gravitationally suspended. In using the apparatus described in the above-referred to patent it is necessary for the patient to stand at the foot of a table, facing the X-ray tube, and bend forward or lean over so as to suspend the breast between tissue embracing walls of the device. Compression force is then applied to the tissue. A standing position is used for both the cephalocaudal view and the lateral-medial views.

While the technique and the apparatus of the above described patent have proven useful and diagnostically valuable, certain shortcomings have now been noted. For example, the angle at which the gravitationally suspended breast of the standing subject depends affects the orientation of the tissue relative to the radiation source used. Only minimal variation or adjustment is feasible, a limitation which has been found significant. The present invention stems from and invokes the concept that the precise physical orientation of the suspended tissue is critical in achieving optimum image fidelity coupled with minimal radiation exposure.

It is a feature of the present invention that the manipulable cradle or body support makes possible positioned gravitational suspension of the breast tissue in each of a series of diverse selectible angles to facilitate definitive, precisely controlled exposure of the tissue in diagnostic radiological procedures.

Another feature of the invention is that it includes a table or cradle which comfortably supports the patient in any medically preferred disposition or spacial orientation so as to minimize patient movement and to obviate patient fatigue.

A related advantage of the invention is that it allows radiation exposures to be taken at varied, yet controlled and reproducible relative angles to provide a more meaningful series of film displays, thereby to enhance the reliability and usefulness of diagnoses.

Yet another advantage of the invention is that a complete series of exposures may be made at extremely low radiation intensities and dosages so as to minimize any potentially hazardous radiation effects.

Yet another important feature of the invention is that it includes means whereby the subject-supporting table may be simply and rapidly manipulated about each of a pair of mutually perpendicular horizontal axes so that any required angle of tissue suspension, relative to the body of the subject, may be easily achieved.

A related feature of the invention is that is includes apparatus whereby tissue contacting and compressing walls may be elevated, shifted, and rotated independently of the body support table itself, thus ensuring complete versatility and ready adaptation in all modes of patient support.

A related feature of the invention is that, by recording the various manipulation, settings and adjustment parameters, the examining physician is able to reproduce precisely a viewing field corresponding to one previously used, so that exact and meaningful comparisons of tissue condition may be made as a function of time.

The present invention makes it possible to examine the breast of a female subject under conditions such that the internal structures are radiographically displayed for diagnostic visualization, in their most orderly anatomic arrangement and under conditions of reduced and substantially uniform tissue thickness to permit minimal radiation exposure and to ensure optimum field of examination, sharp image focus, and more even image density.

It is a feature of the apparatus and method of the invention that it is possible to reduce the intensity of radiation as well to decrease the scattering of radiation energy. It is a general feature of the invention in that it provides an improved technique and apparatus for the diagnostic X-ray examination of the female breast under conditions of complete immobilization of breast tissue, yet without any discomfort to or fatigue of the subject.

A feature of the invention is that the subject-supporting table may be tilted about a horizontal axis in a manner so as to effect minimal lateral disorientational displacement of the patent's subtended breast.

A related feature of the invention is that the subject-supporting table may be pivoted about each of a pair of parallel, laterally-spacial longitudinally-extending axes so as to minimize lateral shifting of the breast as its dependence angle relative to the subject's body is varied.

It is an important feature of the invention that the cooperating elements of the weight-bearing frame are positioned very close to one another so as to establish a pivotal or fulcrum point as close as possible to the estimated center of each breast whereby when the cradle is titled transversely at that fulcrum, movement of the breast relative to the compression device is minimized, requiring minimal adjustment of the X-ray tube and conpression device in changing from one breast to the other.

SUMMARY OF THE INVENTION

The enhanced utility and versatility of the present invention derives from the novel body supporting table or cradle which enables the subject to assume a selectible prone rather than a standing or a sitting position. A substantive feature of the table of the invention is that, rather than being physically fixed, it is readily tiltable forward and rearwardly as well as laterally so that the breast of the patient may be adjusted quickly and simply to any preferred suspension angle as the breast tissue depends freely below the table through a cut-away areal zone in the support surface of the table. Functionally associated with the adjustable table is a radiation source which is so mounted as to be elevatable, horizontally positionable, and rotatable, whereby the radiation beam may be precisely directed to selectible areas of examination. The radiation source may be beamed through full 360° of rotation to facilitate the production of radiographic plates at any preferred incidence or reference angle with respect to the breast tissue.

Physically coupled to and adjustable and rotatable with the radiation source is a compression assembly (described in detail in U.S. Pat. No. 3,578,971) constituting opposed wall means whereby the gravitationally suspended breast of the subject may be subjected to compression forces so as gently to flatten, spread, and shape the breast to establish an optimum field of radiographic examination and to enhance image focus and density under conditions of minimized radiation exposure. Additional general important features of the invention are its simplicity of operation and its reliability in use.

The above and other objects, features, utilities and advantages of the invention will be more clearly understood upon a review of the invention will be more clearly understood upon a review of the detailed description considered with the drawings. The preferred embodiment presented herein is an example only and is not to be considered as limiting the invention in any way.

DESCRIPTION OF THE DRAWINGS

FIG. 3 is a front elevational view of the apparatus;

FIG. 4 is a top plan view of the rotatable and elevatable carriage which supports a radiation source and a structure defining an irradiation chamber;

FIG. 5 is a view taken on the lines 5—5 of FIG. 3 and showing the hydraulic mechanism by which the carriage of FIG. 4 is positioned vertically;

FIG. 6 is a cross sectional view taken substantially on the lines 6—6 of FIG. 3 showing a portion of the shiftable base constituting a part of the carriage assembly on which the radiation source is carried; and FIG. 7 is a diagrammatic representation of the hydraulic control system for manipulating and positioning the body supporting frame, and including a pump, fluid lines, solenoid valves and actuation switches by means of which the frame is adjusted to the desired positions.

DESCRIPTION OF THE PREFERRED EMBODIMENT

In accordance with a preferred embodiment of the invention, the aims and objects are accomplished by providing a table or cradle carrying the entire weight and manipulatively supporting a female subject in a prone position to facilitate the gravitational suspension of the subject's breast in diverse, selectible depending angles relative to the subject's body. The frame-carried body-supporting sheet or web is provided with a forwardly disposed open areal section through which the gravitationally suspended breast depends, and the support table itself is provided with means for pivotal tilting about each of a pair of mutually perpendicular horizontal axes making it possible to suspend the breast in the zone below the table at any preferred angle relative to the body of the subject. The apparatus also includes laterally shiftable wall means defining a breast-accepting upwardly opening irradiation chamber therebetween, and means for shifting the wall means to recede from and approach one another so as to establish selectible spacings correlated with associated compression forces applied by the wall means to the breast disposed therebetween, thereby gently to flatten, spread, and shape the breast to establish an optimum field of radiographic examination and to enhance image focus and density under conditions of minimized radiation exposure. The exemplary device provides, in combination, the novel body supporting structure which is used as an adjunct to and in cooperation with the apparatus for producing the desired compression of the breast while the breast is in a substantially vertical, suspended position. The described use of gravity is a positive aid to ensure a proper and orderly anatomic arrangement coupled with the capability of exposing a precisely selected portion of the breast.

Figure 1:
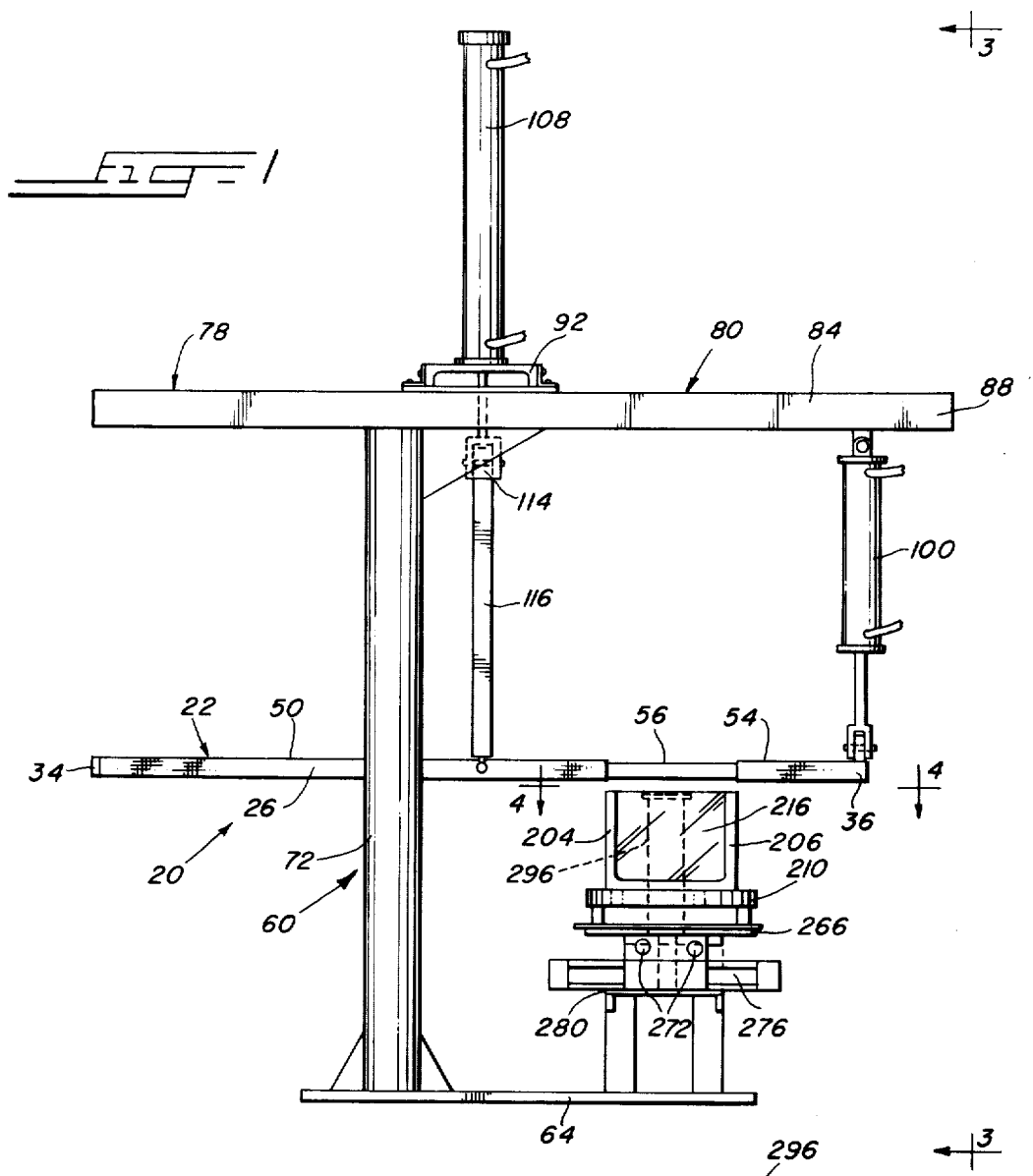
FIG. 1 is a side elevational view of the apparatus of the invention, including the positionable body-supporting frame thereof.
Figure 2:
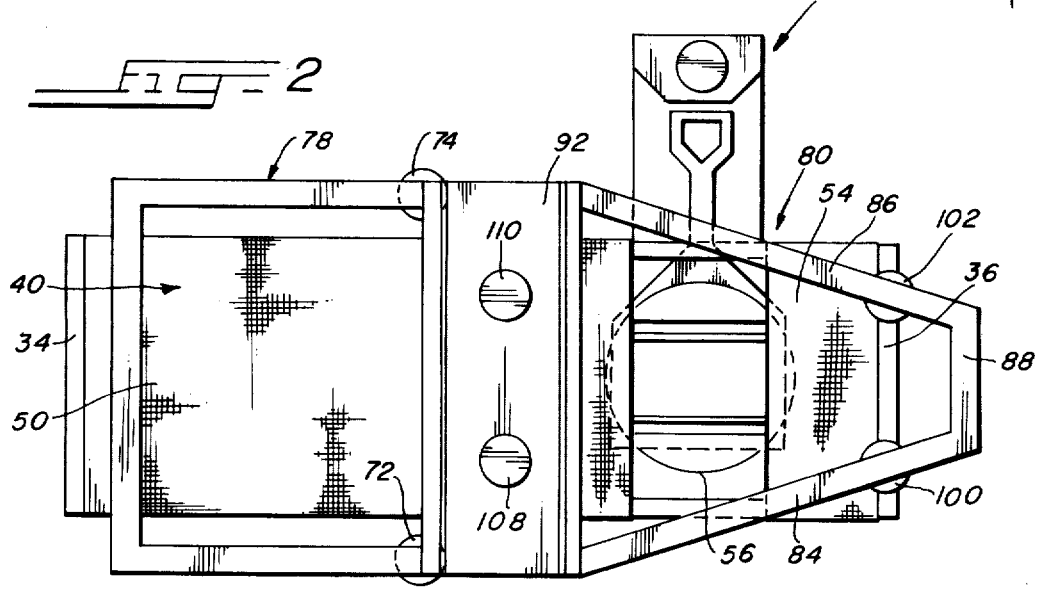
FIG. 2 is a top plan view of the apparatus of FIG. 1.

Referring more particularly to the drawings, there is shown in FIGS. 1, 2 and 3, for the purpose of illustrative disclosure, a preferred embodiment of the manipulable body-supporting table 20 of the invention. In the embodiment illustrated, the table or cradle 20 includes an elongated, generally rectangular frame 22 having a pair of opposed, coextensive, generally parallel, spaced side bars 26 and 28 connected to one another at corresponding opposed ends by means of a pair of rear and forward end bars 34 and 36. A web or sheet 40 of a washable fabric or plastic composition and having high physical strength is stretched to bridge or span the spaced side bars 26 and 28 and substantially to cover the area enclosed by the frame. Preferably, the opposed side bars are slidably sleeved through cooperating elongated loops or channels and formed by folding the marginal portions of the web 40 over the frame elements and stitching or stapling, or otherwise fastening the lateral terminal edges of the web to the web proper along the length thereof. Alternative modes of web securement may be utilized.

In using the apparatus, the subject lies prone upon the frame-carried web 40 so that the major body weight is carried by the principal web component 50, and so that the patient's head and extreme upper portion of the torso are supported on the short, forward web section 54, in which position the patient's breasts hang gravitationally suspended through the open areal section 56.

An essential, fundamental, characterizing feature of the present invention is manipulability of the table 20 for pivotal arcuate movement about each of two mutually perpendicularly horizontal axes. While the specific structure by which such degrees of motion are achieved is not, per se, an essential element of the invention, in the interest of providing a complete disclosure, a preferred mode by which the aims of the invention are carried out is described below with reference to FIGS. 1, 2 and 3. As shown, there is provided a standard 60 consisting of a U-shaped floor plate 64 and a pair of posts or pillars 72 and 74 fastened to and extending upwardly of the floor plate 64. A horizontally extending, U-shaped channel 78 is fastened to the upper ends of the posts 72 and 74 and projects horizontally so as substantially to overlie the floor plate 64.

The forwardly opening U-shaped top channel 78 is connected to an essentially coplanar extension 80 having a pair of inwardly angled sides 84 and 86 bridged and interconnected at their forwardly directed ends by a front cross bar 88. Interconnection and securement of the various component elements of the structural support may be by any preferred technique as by the use of nuts and bolts. However, in the specific embodiment of the invention shown, the parts are joined by welding. The basis structure includes a support channel 92 which is fastened to and bridges the upper U-shaped channel 78 at a position displaced from but generally paralleling the front cross bar 88.

The mechanism by which the table 20 is pivotally tilted about each of two mutually perpendicularly horizontal axes is described with reference to FIGS. 1,2,3 and 6. In the embodiment of the invention depicted, the movement and control mechanisms utilized are fluid-pressure-actuated piston and cylinder assemblies, four such assemblies being employed in the apparatus shown. Hingedly fastened to the forward end bar 36 of the frame 22 at laterally displaced opposed positions are a pair of piston and cylinder assemblies 100 and 102 which extend upwardly from the frame 22 and are hingedly fastened at their upper ends to the overhead channel bars 84 and 86.

A second pair of piston and cylinder assemblies 108 and 110 supported on and hingedly secured to the upper yoke plate 92 are fastened at their lower extremities to a horizontal cross bar 114 bridging the arms 116 and 118 of a U-shaped frame-carrying hanger 122. The lower extremities of the arms 116 and 118 of the hanger 122 are secured respectively to the side bars 26 and 28 of the frame 22. Fluid for actuating the various assemblies is pumped to each through suitable flexible pressure lines or conduits 130 A-D and 132 A-D from a pump and reservoir assembly 134. Selective routing of pressurized fluid to cause extension and retraction of each particular hydraulic assembly is effected through a master panel 138 which, in the specific embodiment of the invention shown includes eight electrical switches 144 E-H and 146 E-H, each switch controlling one or more solonoid valves 150 E-H and 152 E-H regulating the input and exhaust of fluid from each hydraulic mechanism 100, 102, 108, and 110. Many and varied modes of interconnecting the various fluid pressure lines and actuating switches are possible, and those skilled in the art will appreciate that the selection of any particular interconnection arrangement is highly subjective. Moreover, the exact detailed structure of the hydraulic system does not itself constitute a critical element of the present invention. Accordingly, no exhaustive treatment of the system is provided herein. However, for ease of operation and for simplicity, a particular connecting pattern has been adopted in the present invention. The "coding"and the functional responses of switch actuation are described briefly herebelow, and a schematic diagram illustrating the functional interconnections is provided in FIG. 7. In the exemplary apparatus, switches 144 E-H are colored, respectively, green, yellow, blue and red. The same color coding is used for switches 146 E-H, respectively.

Referring now more particularly to the switches 144 E-H, switch 144 E(green) causes energization of those solonoids (input through lines 132 A-D, exhaust through lines 130 A-D) which control the flow of fluid into each of the piston and cylinder assemblies in a manner to cause shortening of each assembly 100, 102 and 108, 110, whereby the table 20 is raised. Switch 146 E (green) is the counterpart of switch 144 E and actuation of the 146E switch actuates solonoids to effect fluid flow so as to elongate each of the piston and cylinder assemblies 100, 102 and 108, 110, (input through lines 130 A-D and exhaust through lines 132 A-D) so that the table 20 is lowered. Switch 144 F (yellow) is operationally effective to cause shortening of the lateral piston and cylinder assemblies 100 and 108 (input to 132 C and 132 A and exhaust through 130 C and 130 A) so that the bed 20 is pivoted about its longitudinal axis in a clockwise direction as viewed from the front end of the apparatus. The counterpart switch, 146 F(yellow) causes extension of each of the piston and cylinder assemblies 100 and 108 (input through 130 C and 130 A and exhaust through 132 C and 132 A) so that the bed 20 is pivoted about its longitudinal axis in a counterclockwise direction as viewed from the front.

Actuation of the switch 144 G (blue) results in a shortening of the lateral piston and cylinder assemblies 102 and 110 (input through 132 D and 132 B and exhaust through 130 C and 130 B) to effect a tilting of the bed 20 about its longitudinal axis in a counterclockwise direction as viewed from the front of the apparatus. The counterpart switch 146 G (blue) causes the piston and cylinder assemblies 102 and 110 to lengthen or extend (input through 130 D and 130 B and exhaust through 132 D and 132 B) thereby affecting pivotal rotation of the bed 20 about its longitudinal axis in a clockwise direction as viewed from the front. Actuation of switch 144 H (red) causes front end piston and cylinder assemblies 100 and 102 to shorten while concurrently causing rear end piston and cylinder assemblies 108 and 110 to lengthen (input through 130A, 130B, 132C and 132D and exhaust through 132A, 130B, 130C and 130D) thereby causing the bed 20 to pivot about a transverse axis in a counter-clockwise direction as viewed fron the near side of FIG. 1. The counterpart switch 146 G(red) causes elongation of the front end piston and cylinder assemblies 100 and 102 while concurrently shortening the rear end piston and cylinder assemblies 108 and 110, (input through 132A, 132B, 130C and 130A and exhaust through 130A, 130B, 132C and 132D) thereby affecting pivotal rotation of the bed 20 about a transverse axis, in a clockwise direction as viewed from the near side of FIG. 1.

It is an important feature of the present invention that the frame 22 is pivotally so supported that tilting or pivotal rotation of the frame about a transverse axis takes place about an axis located in a zone vertically in line with a spacial region delineated by the cut out, open areal section 56 formed in the body-supporting web 40.

This arrangement makes it possible physically to position the gravitationally suspended breast of a subject generally in a zone through which the transverse pivotal axis of the apparatus passes, thereby to minimize longitudinal shifting of the tissue which is being examined radiologically, irrespective of the particular angle at which the breast tissue is suspended relative to the body of the subject.

Additionally, the forward pair of piston and cylinder assemblies 100 and 102 are placed relatively close to a longitudinal midline of the frame 22, as are the rear assemblies 108 and 110, thereby obviating undue lateral shifting of the patient's breasts as the table is adjustably pivoted about a horizontally disposed longitudinal axis. In this way only minimal spacial repositioning of the breast-compressing mechanism and minimal shifting of the X-ray tube are required in shifting examination of one breast to the other.

It is another important feature of the present invention that there is provided, in conjunction with the support apparatus facilitating gravitational suspension of the breast of a subject in a series of selectible varied angles, cooperating apparatus whereby compression forces may be applied, laterally, to the breast, gently to flatten, spread, and shape the breast to establish an optimum field of radiographic examination and to enhance image focus and density under conditions of minimized radiation exposure. Such apparatus is shown in and is described briefly with reference to FIG. 3. The compression apparatus 200 includes a pair of laterally spaced, generally parallel, walls 204 and 206 carried by and extending upwardly from a horizontal base plate 210. The walls 204 and 206 are made of radiation-transparent materials, clear, rigid plastic sheets of polyalkylacrylate (lucite or Plexiglass) being preferred. The plastic walls 204 and 206 are carried in suitable frames 212 and 214, one frame 212 being fixed in position with respect to the base plate 210, and the other frame 214 being shiftable or movable to selectible positions nearer and farther from the fixed frame 212. The frame-carried walls 204 and 206 define therebetween a zone or irradiation chamber 216 in which the breast is gravitationally suspended while the walls engage to sandwich and compress the tissue.

In use, an X-ray-sensitive material 220, in a suitable container may be placed between the breast and the fixed plastic sheet 204, which would serve as a support, or the X-ray-sensitive material 220 may be placed outside the fixed compression sheet 204, according to the recording medium selected and the desired coverage. The movable sheet 206 provides the compression and locks in position, and the radiographic film 220 is exposed through the compressing sheet 206 by the horizontally projected X-ray beam eminating from an X-ray source 230.

Any preferred mechanical means may be utilized in effecting the controlled movement or lateral displacement of the movable plastic wall 204. In the form of the device illustrated, the compression apparatus 200 includes horizontally extending slide rods or guides 236 which extend through and slidably support the laterally shiftable frame 214. Stabilization of the shiftable frame 214 to preclude pivotal rotation about its lower edge is effected by means of auxiliary struts or arms 240 fastened at their upper ends to the side walls of the frame 214 and projecting downwardly and outwardly and terminating at their lower ends in bearings or wheels 244 which also ride in tracks.

The shiftable frame 214 is secured in any selectible lateral position along the slide rods 236 by means of a locking device which may take any preferred form.

The manner in which the base plate 210 and the compression wall assembly 200 supported thereon are positioned with reference to the gravitationally suspended breast of the patient is described with reference to FIGS. 3 and 6. As shown, the base plate 210 is carried on and secured to an undercarriage assembly 260 which includes a ring bearing rotatably mounted on a turntable ring 266. The turntable ring 266 is mounted on a duo-directional slideway assembly 270 including one set of horizontally projecting slide bars 272 generally paralleling a longitudinal axis of the frame 22 on which the patient is supported, and a second set of slide rods 276 located beneath the first, projecting horizontally but extending normally to the first set of slide bars 272. Suitable locking means such as friction clamps are provided to retain the slideway assembly secured in any elected cordinate position.

The slideway assembly 270 and the surmounting turntable 266 and a supporting platform 280 are secured to a horizontal arm 284 fastened to a vertically extending rod 290 of a piston and cylinder assembly 296 so that the undercarriage assembly 260 including the ring 266 mounted thereon may be moved to any desired elevation, thereby to bring the tissue confining and embracing walls 204 and 206 to a height or level where they may functionally be positioned to encompass the spacial zone into which the gravitationally depending breast depends. As described, the entire undercarriage assembly may be controllably shifted laterally, along either or each of two mutually perpendicularly horizontal axes to assume any precise location within the bounds of a horizontal planar area below the open areal section 56 in the frame 22.

The rotatable ring platform 266 also supports the radiation source or gun 230 the output of which is beamed to or directed toward the radiation chamber 216 bracketed by the upstanding compression walls 204 and 206, so that there is maintained a relatively fixed functional orientation between the radiation source 230 and the irradiating chamber 216. Thus the platform 266 is rotatable, is laterally positionable and is adjustable in elevation, thus being readily and quickly oriented to assume any desired position relative to the zone in which the subject's breast is gravitationally suspended. Accordingly, radiographic exposures may be carried out effectively around a full 360° circuit while the breast is suspended at any preferred medically-dictated angle, thus imparting a valuable versatility and diagnostic capability not heretofore achievable.

In the light of the instant disclosure, many structural variations suitable as alternatives to the specific physical embodiment of the invention illustrated will occur to those skilled in the art. For example, as a substitute for the strut suspension system which carries the patient-supporting table, one may elect to use extendable and contractible legs or posts. As still another alternative one may use as a frame support a pillar surmounted by a ball and socket "swivel" structure. Similarly, the particular structural elements and techniques for shifting, rotating, and elevating the X-ray source and the tissue confining wall assembly may take other forms. None of the above suggested or any other structural modifications or variations pertain to the substance of the instant invention. All such arbitrary modifications are deemed to be equivalents within the scope of the appended claims. Moreover, it is intended that all matter contained in the above description or shown in the accompanying drawings shall be interpreted as illustrative and not in a limiting sense.

What is claimed is:

1. The combination with radiation apparatus including a radiation source for presentation to body tissue to be examined, and means responsive to radiations from said radiation source to provide a visual image of said tissue, of a shiftable cradle for manipulatively supporting a female subject in a prone position to facilitate the gravitational suspension of the subject's breast in diverse selectible depending angles relative to the body of the subject, said cradle comprising an elongated frame including a pair of opposed, coextensive, generally parallel bar means, and strut means retaining said bar means apart and fixed relative to each other to maintain a spacial span therebetween, body-support sling means bridging said parallel bar means and secured thereto along the opposed lengths thereof, said sling means being formed with an open areal section extending at least partially transversely thereacross at a position intermediate forward and rearward extremities of said frame, said open areal section being adapted to receive therethrough a gravitationally suspended breast depending from the body of a subject supported on said sling means to present the breast into a zone below said cradle and accessible to a radiated beam eminating from the radiation source and directed toward the breast, frame tilting means operatively connected to said frame for arcuately adjustably pivoting said frame to vary the spacial orientation thereof, said tilting means including means for arcuately pivoting said frame about each of two different axes, said tilting means thereby rendering feasible the suspension of the breast in the zone below said cradle at diverse selectible angles relative to the body of the subject, whereby fidelity and diagnostic value of film images produced in radiographic mammography procedures carried out on the breast of the subject are enhanced.

2. The structure as set forth in claim 1 wherein the axes about which said frame is pivotal constitute a pair of mutually perpendicular axes.

3. The structure as set forth in claim 1 wherein said frame tilting means comprises first and second, extendable and contractible strut means coupled to said frame and operative to pivot said frame about each of a pair of axes.

4. The structure as set forth in claim 3 wherein said extension and contraction strut means for pivotally articulating said frame includes piston and cylinder assemblies, a first of said assemblies being operatively connected for pivoting said frame about a longitudinal axis thereof, and a second of said assemblies being operatively connected for pivoting said frame about a transverse axis thereof.

5. The structure as set forth in claim 4 wherein the transverse axis about which said frame is pivotal lies in a spacial zone beneath said sling means and below the open areal section thereof through which the subject's breast is suspended, whereby the transverse rotational axis of said cradle defines a line passing through a zone in which the subject's breast is suspended.

6. The structure as set forth in claim 1 wherein said frame tilting means comprises four frame-elevating and lowering assemblies, and coupling means mechanically securing said assemblies to said frame, said coupling means including first linkage means anchoring two of said assemblies to said frame on opposite sides of a longitudinally extending midline of said frame and forwardly of said open areal section of said sling means, and second linkage means anchoring two of said assemblies to said frame on opposite sides of a longitudinally extending midline of said frame and rearwardly of said open areal section of said sling means.

7. The structure as set forth in claim 6 and further comprising means for actuating said assemblies in selectible pairs, thereby to raise and to lower each end of said frame, to raise and to lower each side of said frame, and including means for actuating all assemblies simultaneously to raise and to lower said frame, thereby to position the body of the subject supported on said frame in proper position for radiological examination of the breast as the breast is gravitationally suspended.

8. The structure as set forth in claim 1 and further comprisng a breast-restraining assembly consisting essentially of vertically extending, laterally spaced, opposed wall means defining an upwardly opening irradiation chamber therebetween, said wall means being disposed at a level below said sling means and substantially in vertical alignment with said open areal section thereof, whereby a gravitationally suspended breast of a subject supported on said sling means depends into said chamber and between said wall means, means for shifting said wall means to approach and to recede from one another to establish selectible spacings correlated with associated compression forces applied by said wall means to the breast positioned therebetween, thereby gently to flatten, spread, and shape the breast to establish an optimum field of radiographic examination and to enhance image focus and density under conditions of minimized radiation exposure.

9. The structure as set forth in claim 8 and further comprising means for adjusting the elevation of said wall means and means for rotating said wall means about a vertical axis to facilitate engagement of said wall means at selectible opposed areas of a subject's breast gravitationally suspended to depend downwardly between said wall means, thereby to ensure proper placement of the breast for display during radiographic exposure.

10. The structure as set forth in claim 8 and further comprising means for shifting said wall means in a horizontal plane to enhance precise positioning of a subject's breast between said wall means and to ensure proper placement for radiographic display.

11. The structure as set forth in claim 8 and further comprising means for shifting said wall means in a horizontal plane and means for rotating said wall means about a vertical axis, thereby to facilitate engagement of said wall means, with a subject's breast at selectible opposed lateral surface areas thereof to achieve precise positioning and placement for radiographic exposure in a radiographic examination procedure.

12. The structure as set forth in claim 8 and further comprising carriage means disposed beneath said cradle, traverse means for moving and positioning said carriage means in a horizontal plane, and means securing said wall means to said carriage means for support thereon and movement therewith, said carriage means facilitating the positioning of the irradiation chamber operationally to receive a subject's breast and to ensure optimal placement within the chamber for radiographic display during radiographic exposure.

13. The structure as set forth in claim 12 wherein said carriage means also constitutes support means for a source of radiation beam, which beam is to be directed toward the breast of a subject to be examined radiologically.

14. The structure as set forth in claim 13 wherein said wall means and said support means for a source of a radiation beam are carried on said carriage means in attitudes which are fixed relative to one another, whereby energy radiated by the beam source maintains a predetermined orientation with respect to the wall means toward which the beam is directed in a radiographic procedure.

15. The structure as set forth in claim 12 and further comprising means for raising and for lowering said carriage means and said wall means carried thereby.

16. In radiation apparatus including a radiation source for presentation to body tissue to be examined, and means responsive to radiations from said radiation source to provide a visual image of said tissue, and table means for supporting a patient to be subjected to the radiation source, the improvement comprising means for pivotally shifting said table about each of a pair of mutually perpendicular axes for manipulatively positioning a female subject supported on said table, thereby to facilitate the gravitational suspension of the subject's breast in diverse selectable depending angles relative to the subject's body.

17. The improvement as set forth in claim 16 wherein said table means is formed with an open areal section extending at least partially transversely thereacross at a position intermediate forward and rearward extremities thereof, said open areal section being adapted to receive therethrough a gravitationally suspended breast depending from the body of a subject supported on said table means to present the breast into a zone below said table means and accessible to a radiated beam eminating from the radiation source and directed toward the breast.

18. The structure as set forth in claim 1 wherein said tilting means includes means for arcuately pivoting said frame about each of three different axes consisting of two longitudinal axes and a transverse axis.

19. The structure as set forth in claim 18 wherein the axes about which frame is pivotal include two mutually perpendicular axes.

* * * * *